(12) United States Patent
Bleckmann et al.

(10) Patent No.: US 6,653,397 B2
(45) Date of Patent: Nov. 25, 2003

(54) PREPARATIONS OF THE W/O EMULSION TYPE WITH AN INCREASED WATER CONTENT, COMPRISING MODERATELY POLAR AND/OR NONPOLAR LIPIDS AND ONE OR MORE INTERFACE-ACTIVE POLYETHERS OF THE A-O-B-O-A TYPE, AND COMPRISING AT LEAST ONE SUBSTANCE CHOSEN FROM THE GROUP OF CATIONIC POLYMERS

(75) Inventors: Andreas Bleckmann, Ahrensburg (DE); Rainer Kröpke, Schenefeld (DE)

(73) Assignee: Beiersdorf AG, Hamburg (DE)

( * ) Notice: Subject to any disclaimer, the term of this patent is extended or adjusted under 35 U.S.C. 154(b) by 215 days.

(21) Appl. No.: 09/961,912

(22) Filed: Sep. 24, 2001

(65) Prior Publication Data

US 2002/0082327 A1 Jun. 27, 2002

(30) Foreign Application Priority Data

Sep. 29, 2000 (DE) .......................... 100 48 366

(51) Int. Cl.$^7$ ........................... C08L 71/02; C08L 71/08
(52) U.S. Cl. ...................... 524/801; 524/376; 524/474; 524/593
(58) Field of Search ................. 524/801, 593, 524/474, 376

(56) References Cited

U.S. PATENT DOCUMENTS 6,060,042 A     5/2000   Schuhmacher et al. ....... 424/60

FOREIGN PATENT DOCUMENTS

| DE | 43 44 697 A1 | 6/1995 | |
|---|---|---|---|
| DE | 43 45 186 A1 | 6/1995 | |
| DE | 43 12 656 C2 | 1/1996 | |
| DE | 195 01 288 A1 | 7/1996 | |
| DE | 196 43 237 A1 | 4/1998 | |
| DE | 196 43 238 A1 | 4/1998 | |
| EP | 0 586 106 B1 | 1/1997 | |
| EP | 0549 592 B1 | 8/1998 | |
| EP | 0 962 222 A2 | 8/1999 | ............ A61K/7/42 |
| WO | WO 99/26587 | 6/1999 | |

OTHER PUBLICATIONS

Adam, Wolfgang E. ; "Neue Polyalkylenglykol–Copolymere für die Kosmetik"; Seifen—Öle—Fette—Wachse—110.Jg.—Nr. 15/1984, pp. 427–431.

Primary Examiner—Peter Szekely
(74) Attorney, Agent, or Firm—Norris McLaughlin & Marcus

(57) ABSTRACT

A water-in-oil emulsion (a) with a content of water and optionally water-soluble substances totaling at least 70% by weight, and with a content of lipids, emulsifiers and lipophilic constituents totaling at most 20%, in each case based on the total weight of the preparations, (b) with a lipid phase whose total polarity is between 20 and 45 mN/m, (c) comprising at least one interface-active substance chosen from the group of substances of polyethers of an oligomeric or polymeric molecular unit B, the monomers of which are branched or unbranched α, ω-alkylene glycols (α, ω-dihydroxyalkanes) having 3–25 carbon atoms and
two units A composed of polyoxyethylene groups, where the molecular units A and B are linked together according to the scheme A-O-B-O-A via ether groups, (d) comprising at least one substance chosen from the group of cationic polymers.

12 Claims, No Drawings

PREPARATIONS OF THE W/O EMULSION TYPE WITH AN INCREASED WATER CONTENT, COMPRISING MODERATELY POLAR AND/OR NONPOLAR LIPIDS AND ONE OR MORE INTERFACE-ACTIVE POLYETHERS OF THE A-O-B-O-A TYPE, AND COMPRISING AT LEAST ONE SUBSTANCE CHOSEN FROM THE GROUP OF CATIONIC POLYMERS

The present invention relates to cosmetic and dermatological preparations, in particular those of the water-in-oil type, to processes for their preparation and to their use for cosmetic and medicinal purposes.

The present invention relates, in a particular embodiment, to cosmetic or pharmaceutical preparations with an improved feel on the skin, reduced feeling of stickiness, to processes for their preparation, and to the use of active ingredients for reducing the feeling of stickiness of cosmetic preparation.

The human skin is man's largest organ and performs a number of vital functions. Having an average surface area of about 2 m² in adults, it has a prominent role as a protective and sensory organ. The purpose of this organ is to transmit an average mechanical, thermal, actinic, chemical and biological stimuli. In addition, it has an important role as a regulatory and target organ in human metabolism.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist its horny layer in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin aging.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally taken to mean heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil, and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable W/O preparations for cosmetic or dermatological use, for example in the form of creams and ointments which can be spread in the range from room temperature to skin temperature, or as lotions and milks, which are more likely flowable in this temperature range. However, there are not many formulations in the prior art which are of sufficiently low viscosity that they would, for example, be sprayable.

In addition, low-viscosity preparations of the prior art frequently have the disadvantage that they are unstable, and are limited to a narrow field of application or a limited choice of feed materials. Low-viscosity products in which, for example, strongly polar oils—such as the plant oils otherwise frequently used in commercially available products—are sufficiently stabilized are therefore currently not on the market.

The term "viscosity" means the property of a liquid to resist the mutual laminar displacement of two neighboring layers (internal friction). This so-called dynamic viscosity is nowadays defined according to $\eta = \tau/D$ ad the ratio of shear stress to the velocity gradient perpendicular to the direction of flow. For Newtonian liquids, $\eta$ is a material constant having the SI unit Pascal second (Pa.s) at a given temperature.

The quotient $v = \eta/\rho$ from the dynamic viscosity $\eta$ and the density $\rho$ of the liquid is referred to as the kinematic viscosity $v$ and is given in the SI unit m²/s.

Fluidity ($\phi$) is the inverse of viscosity ($\phi = 1/\eta$). In the case of ointments and the like, the use value is inter alia co-determined by the so-called tack. The tack of an ointment or ointment base or the like is understood as meaning its property to draw threads of varying lengths when a small sample is removed; accordingly, a distinction is made between short- and long-stretch substances.

Whilst the graphical representation of the flow behavior of Newtonian liquids at a given temperature produces a straight line, in the case of the so-called non-Newtonian liquids considerable deviations often arise, depending on the respective velocity gradient D (shear rate $\gamma$) or the shear stress $\tau$. In these cases, the so-called apparent viscosity can be determined which although it does not obey the Newtonian equation, can be used to determine the true viscosity values by graphical methods.

Falling-body viscometry is suitable only for investigating Newtonian liquids and gases. It is based on Stokes's law, according to which for the falling of a sphere through a liquid which flows around it, the dynamic viscosity $\eta$ can be determined from:

$$\eta = \frac{2r^2(\rho_k - \rho_{Fl})g}{9 \cdot v}$$

where
r=radius of the sphere, v=fall velocity, $\rho_K$=density of the sphere, $\rho_{F1}$=density of the liquid, and g=acceleration of fall.

W/O emulsions with a high water content and a low viscosity which moreover have storage stability, as is required for marketable products, can only be formulated according to the prior art in a very complex manner. Accordingly, the supply of formulations of this type is extremely low. Nevertheless, such formulations have been able to offer the consumer hitherto unknown cosmetic effects.

One object of the present invention was to provide preparations which have a very low viscosity and do not have the disadvantages of the prior art.

A further object of the present invention was to provide preparations which can be laden with a high content of water-soluble and/or water-miscible substances having cosmetic or dermatological effectiveness, without impairing the galenical quality or other properties of the preparations.

Although it is known that the addition of certain substances, for example some selected powder raw materials, in particular talc, reduces this feeling of stickiness or else feeling of greasiness, apart from the fact that this is only rarely achieved completely, such an addition also changes the viscosity of the product in question and reduces the stability.

A further object was therefore to overcome all of these disadvantages of the prior art. In particular, the aim was to provide products with reduced stickiness or greasiness. Products in the field of care cosmetics, decorative cosmetics and pharmacological galenics were likewise to be freed from the described disadvantages of the prior art.

It was a further object of the invention to develop cosmetic bases for cosmetic preparations which are characterized by good skin compatibility.

It was a further object of the present invention to provide products which have the broadest possible diversity of use. For example, it was the aim to provide bases for preparation forms such as cleansing emulsions, face care and body care preparations, but also distinctly medicinal-pharmaceutical presentations, for example preparations against acne and other skin conditions.

According to K. J. Lissant: *The Geometry of High-Internal-Phase-Ratio Emulsions;* Journal of Colloid and Interface Science 22, 462–468 (1966), emulsions with an internal phase of more than 70% are defined as so-called high internal phase emulsions. The preparation of stable, flowable water-in-oil emulsions with a water content of more than 70% is very difficult. In particular, "high internal phase" W/O emulsions with a very high water content of more than 85% ("very high internal phase" W/O emulsions) are not accessible.

The technique of varying the phase volume ratio (i.e. incorporating higher amounts of liquid lipids) which is usually used for water-in-oil emulsions can, because of the low lipid content, be used only to a limited extent in the case of high internal phase W/O emulsions, or not at all in the case of very high internal phase W/O emulsions. For this reason, only water-in-oil emulsions with a solid to semisolid consistency are accessible. Even the use of polar lipids, which usually give water-in-oil emulsions of lower viscosity, does not lead to the desired success.

Surprisingly, it has been found that water-in-oil emulsions
(a) with a content of water and optionally water-soluble substances totaling at least 70% by weight, and with a content of lipids, emulsifiers and lipophilic constituents totaling at most 20%, in each case based on the total weight of the preparations,
(b) with a lipid phase whose total polarity is between 20 and 45 mN/n,
(c) comprising at least one interface-active substance chosen from the group of substances of polyethers of an oligomeric or polymeric molecular unit B, the monomers of which are branched or unbranched α, ω-alkylene glycols (α, ω-dihydroxyalkanes) having 3–25 carbon atoms and
two units A composed of polyoxyethylene groups,
where the molecular units A and B are linked together according to the scheme A-O-B-O-A via ether groups,
(d) comprising at least one substance chosen form the group of cationic polymers overcome the disadvantages of the prior art.

The polyoxyethylene component preferably has the following basic structure:

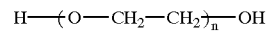

where n can advantageously assume values from 10–200. Polyoxyethylene entities with 20–70 oxyethylene units are particularly advantageous.

The component of the branched or unbranched α, ω-alkylene glycols preferably has the following basic structure:

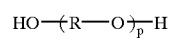

where the group $(-R-O-)_p$ will also be referred to below by the symbol R, p typically assumes values between 2 and 200.

The copolymers advantageous according to the invention are obtainable, for example, by reactions according to the following scheme:

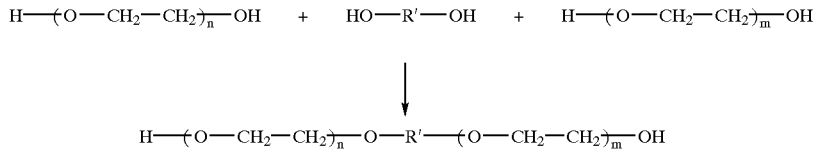

where n and m, independently of one another, can advantageously assume values from 10–200. Polyoxyethylene entities with 20–70 oxyethylene units are particularly advantageous.

For the purposes of the present invention, the polyethers listed in the Chemical Abstracts with the registry number 78336-31-9, which carry the chemical name polyethylene glycol di(polydodecylene glycol) ethers and are sold, for example, as PEG-45 (dodecyl glycol)copolymer under the name Elfacos® ST 9 (average molecular weight about 4000 g/mol) and as PEG-22 (dodecyl glycol) copolymer under the name Elfacos® ST 37 (average molecular weight about 2300 g/mol) by Akzo Nobel Chemicals GmbH, are particularly advantageous.

The total amount of interface-active polyethers used according to the invention in the finished cosmetic or dermatological preparations is advantageously chosen from the range 0.1–30% by weight, preferably 0.25–5.0% by weight, in particular 0.75–3.5% by weight, based on the total weight of the preparations.

Although it is known that W/O emulsions can be produced using emulsifiers of the type described previously, the known prior art was nevertheless unable to indicate the route to the present invention.

For the purposes of the present invention, examples of suitable cationic polymers are: Cationic cellulose derivatives (e.g. Polymer JR 400® from Amerchol), cationic starch, copolymers of diallylammonium salts and acrylamides, quaternized vinylpyrrolidone/vinylimidazole polymers (e.g. Luviquat® from BASF), condensation products of polyglycols and amines, quaternized collagen polypeptides (e.g. Lamequat® L from Grünau-Henkel), quaternized wheat polypeptides, polyethyleneimine, cationic silicone polymers, copolymers of adipic acid with dimethylamino-hydroxypropyldiethylenetriamine, copolymers of acrylic acid with dimethyldiallylammonium chloride (e.g. Merquat® 550 from Chemviron), polyaminopolyamides, cationic chitin derivatives, cationic guar gum (e.g. Jaguar® CBS from Hoechst Celanese), quaternized ammonium salt polymers (e.g. Mirapol® AD-1 from Miranol), and cationic biopolymers such as, for example, chitosan (average molecular weight from 50 000 to 2 000 000 g/mol [determined by means of gel permeation chromatography] and a degree of deacylation of from 10 to 99% [determined by means of $^1$H-NMR]).

Chitosan is a partially deacylated chitin. This biopolymer has inter alia film-forming properties and is characterized by a silky feel on the skin. However, a disadvantage is its severe stickiness on the skin which arises, in particular, temporarily during use. In individual cases, it may then be possible that corresponding preparations are not marketable since they are unaccepted or viewed negatively by the consumer. As is know, chitosan is used, for example, in hair care. It is suitable, to a better degree than the chitin on which it is based, as a thickener or stabilizer and improves the adhesion and water resistance of the polymeric films. Representative of a large number of references of the prior art: H. P. Fiedler, "Lexikon der Hilfsstoffe für Pharmazie, Kosmetik und angrenzende Gebiete", [Lexicon of auxiliaries of pharmacy, cosmetics and related fields], third edition 1989, Editio Cantor, Aulendorf, p. 293, keyword "Chitosan".

Chitosan is characterized by the following structural formula:

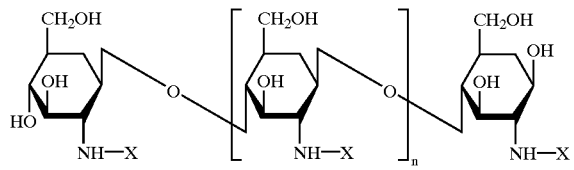

where n assumes values of up to about 10 000, X is either the acetyl radical or hydrogen. Chitosan is formed by deacetylation and partial depolymerization (hydrolysis) of chitin, which is characterized by the structural formula:

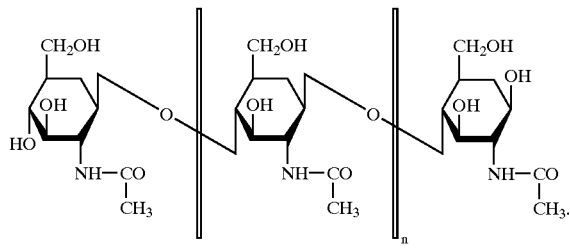

Chitin is an essential constituent of the exoskeleton [τοχιτων=Greek for integument] of arthropods (e.g. insects, crabs, spiders) and is also found in supporting tissue of other organisms (e.g. mollusks, algae, fungi).

In the range of about pH<6, chitosan is positively charged and is also soluble in aqueous systems at this pH. It is not compatible with anionic raw materials. For this reason, to prepare chitosan-containing oil-in-water emulsions, the use of nonionic emulsifiers is appropriate. These are known per se, for example from EP-A 776 657.

The total amount of cationic polymers used according to the invention in the finished cosmetic or dermatological preparations is advantageously chosen from the range 0.1–30% by weight, preferably 0.25–5.0% by weight, in particular 0.75–3.5% by weight, based on the total weight of the preparations.

Surprisingly, it has been found, in particular, that by adding cationic polymers it is possible to prepare the stable, flowable "very high internal phase emulsions" which have excellent sensory properties.

In some instances, it may also be advantageous to additionally use a content of anionic and/or amphoteric and/or nonionic polymers, the total amount of such polymers in the finished cosmetic or dermatological preparations advantageously being chosen from the range 0.1–30% by weight, preferably 0.25–5.0% by weight, in particular 0.75–3.5% by weight, based on the total weight of the preparations.

For the purposes of the present disclosure, a general term for fats, oils, waxes and the like which is sometimes used is the term "lipids", with which the person skilled in the art is entirely familiar. The terms "oil phase" and "lipid phase" are also used synonymously.

Oils and fats differ from one another in their polarity, which is difficult to define. It has already been proposed to adopt the interfacial tension towards water as a measure of the polarity index of an oil or of an oil phase. This means that the lower the interfacial tension between this oil phase and water, the greater the polarity of the oil phase in question. According to the invention, the interfacial tension is regarded as one possible measure of the polarity of a given oil component.

The interfacial tension is the force which acts on an imaginary line of one meter in length in the interface between two phases. The physical unit for this interfacial tension is conventionally calculated from the force/length relationship and is usually expressed in mN/m (millinewtons divided by meters). It has a positive sign if it endeavors to reduce the interface. In the converse case, it has a negative sign.

Table 1 below lists moderately polar lipids which are advantageous according to the invention as individual substances or else as mixtures with one another. The interfacial tensions towards water concerned are given in the last column. It is, however, also advantageous to use mixtures of higher and lower polarity and the like, provided it is ensured that the total polarity of the oil phase is within the claimed range.

TABLE 1

| Trade name | INCI Name | (mN/m) |
| --- | --- | --- |
| Isofol ™ 14 T | Butyl Decanol + Hexyl Decanol + Hexyl Octanol + Butyl Octanol | 27.6 |
| Isofol ® 16 | Hexyl Decanol | 24.3 |
| Eutanol ® G | Octyldodecanol | 24.8 |
| Cetio ® OE | Dicaprylyl Ether | 22.1 |
| Miglyol ® 812 | Caprylic/Capric Triglyceride | 21.3 |
| Cegesoft ® C24 | Octyl Palmitate | 23.1 |
| Isopropyl stearate | Isopropyl Stearate | 21.9 |
| Estol ® 1540 EHC | Octyl Octanoate | 30.0 |
| Finsolv ® TN | $C_{12-15}$ Alkyl Benzoate | 21.8 |
| Cetiol ® SN | Cetearyl Isononanoate | 28.6 |
| Dermofeel ® BGC | Butylene Glycol Caprylate/Caprate | 21.5 |
| Trivent ® OCG | Tricaprylin | 20.2 |

TABLE 1-continued

| Trade name | INCI Name | (mN/m) |
| --- | --- | --- |
| MOD | Octyldodecyl Myristate | 22.1 |
| Cosmacol ® ETI | Di-$C_{12-13}$ Alkyl Tartrate | 29.4 |
| Miglyol ® 829 | Caprylic/Capric Diglyceryl Succinate | 29.5 |
| Prisorine ® 2036 | Octyl Isostearate | 29.7 |
| Tegosoft ® SH | Stearyl Heptanoate | 28.7 |
| Abil ® Wax 9840 | Cetyl Dimethicone | 25.1 |
| Cetiol ® LC | Coco-Caprylate/Caprate | 24.8 |
| IPP | Isopropyl Palmitate | 22.5 |
| Luvitol ® EHO | Cetearyl Octanoate | 28.6 |
| Cetiol ® 868 | Octyl Stearate | 28.4 |

The limit above which an oil phase is regarded as "nonpolar" is generally considered to be about 30 mN/m.

Nonpolar oils which have proven particularly advantageous are the following nonpolar lipids liquid at room temperature: hydrocarbons (mineral oils, cycloparaffin, polyisobutenes, polydecenes) nonethoxylated or propoxylated ethers (caprylyl ether/Cetiol OE) and silicone oils (dimethicones, cyclomethicones, dimethiconol).

According to the above definition of polarity, silicone oils are not regarded as nonpolar, but usually fall into the moderately polar region (typically between 20 and 30 mN/m).

According to the invention, it is possible to tolerate a certain proportion of polar lipids, i.e. those of a polarity less than 20 mN/m in the lipid mixture, but in no case should this proportion exceed 25% by weight, is preferably less than 15% by weight and should ideally be not more than ≦10% by weight, based on the total lipid phase.

According to the teaching presented herewith, W/O emulsions are obtainable whose viscosity at 25° C. is less than 5000 mPa.s (=millipascal seconds), in particular less than 4000 mPa.s, preferably less than 3500 mPa.s (HAAKE Viscotester VT-02).

The oils according to the invention are likewise advantageously chosen from the group of paraffin oils, polylolefins and Vaseline (petrolatum). Of the polyolefins, polydecenes and hydrogenated polyisobutene are the preferred substances.

For the purposes of the present invention, the oil phase can additionally—provided the features listed in the patent claims are considered—advantageously comprise substances chosen from the group of esters of saturated and/or unsaturated, branched and/or unbranched alkanecarboxylic acids having a chain length of from 3 to 30 carbon atoms, and saturated and/or unsaturated, branched and/or unbranched alcohols having a chain length of from 3 to 30 carbon atoms, and saturated and/or unsaturated, branched and/or unbranched alcohols having a chain length of from 3 to 30 carbon atoms and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, such as, for example, jojoba oil.

The oil phase can also be chosen advantageously from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

If desired, fatty and/or wax components which are to be used in the oil phase—as secondary constituents in a minor amount—can be chosen from the group of vegetable waxes, animal waxes, mineral waxes and petrochemical waxes. Examples which are favorable according to the invention are candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes and microcrystalline waxes.

Other advantageous fatty and/or wax components are chemically modified waxes and synthetic waxes such as, for example, those obtainable under the trade names Syncrowax HRC (glyceryl tribehenate), Syncrowax HGLC ($C_{16-36}$-fatty acid triglyceride) and Syncrowax AW 1C ($C_{18-36}$-fatty acid) from CRODA GmbH, and also montan ester waxes, Sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane.

If desired, the fatty and/or wax components can be present either individually or as a mixture.

Any desired mixtures of such oil and wax components can also be used advantageously for the purpose of the present invention. In some instances, it can also be advantageous to use waxes, for example cetyl palmitate, as the lipid component of the oil phase.

Of the hydrocarbons, paraffin oil, hydrogenated polyolefins (e.g. hydrogenated polyisobutene), squalane and squalene can be used advantageously for the purposes of the present invention.

According to the invention, emulsions which are particularly advantageous are those which are characterized in that the oil phase consists of at least 50% by weight, preferably of more than 75% by weight, of at least one substance chosen from the group consisting of Vaseline (petrolatum), paraffin oil and polyolefins, and of the latter, preference is given to polydecenes.

The oil phase can advantageously additionally have a content of cyclic or linear silicone oils or consist entirely of such oils, although it is preferable to use an additional content of other oil phase components apart from the silicone oil or the silicone oils.

Cyclomethicone (octamethylcyclotetrasiloxane) can be used advantageously. However, other silicone oils can also be used advantageously for the purposes of the present invention, for example hexamethylcyclotrisiloxane, polydimethylsiloxane and poly(methylphenylsiloxane).

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ethers, diethylene glycol monomethyl or monoethyl ethers and analogous products, and also alcohols of low carbon number e.g. ethanol, isopropanol, 1,2-propanediol and glycerol, and, in particular, one or more thickeners which maybe chosen from the group consisting of silicon dioxide, aluminum silicates, polysaccharides and derivatives thereof, e.g. xanthan gum, hydroxypropylmethylcellulose.

A particular advantage of the present invention is that it permits high concentrations of polyols, in particular glycerol, to be used.

Particularly advantageous preparations are also obtained when antioxidants are used as additives or active ingredients. According to the invention, the preparations advantageously comprise one or more antioxidants. Antioxidants which are favorable but which are nevertheless optional may be all antioxidants which are customary or suitable for cosmetic and/or dermatological applications.

The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, ψ-lycopene) and their derivatives, lipoic acid and its derivatives (e.g. dihydrolipic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (e.g. buthionine sulfoximines, homocysteine sulphoximine, buthionine sulfones, penta-, hexa-, heptathionine sulfoximines) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid,), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, ferulic acid and its derivatives, butylated hydroxytoluene, butylated hydroxyanisole, nordihydroguaiacic acid, nordihydroguaiareticic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active ingredients which are suitable according to the invention.

For the purpose of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and its derivatives and vitamin A and its derivatives.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a coloring action, thickeners, surface-active substances, emulsifiers, emollients, moisturizers and/or humectants, antiinflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulfates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulfate, zinc sulfate and mixtures thereof.

Corresponding requirements apply mutatis mutandis to the formulation of medicinal preparations.

The W/O emulsions according to the invention can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

Accordingly, for the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorocarbons and chlorofluorocarbons (CFCs).

Also favorable are cosmetic and dermatological preparations which are in the form of a sunscreen. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention contain UV-B filter substances, the latter may be oil-soluble or water-soluble. Examples of oil-soluble UV-B fillers which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate; derivatives of 1,3,5-triazine, preferably 2,4,6-trianilino(p-carbo-2'-ethyl-1'-hexyloxy)-1,3,5 -triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminum, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number of with fatty acids;

alcohols, diols or polyols of low carbon number, and their ethers, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, borage oil or currant seed oil, fish oils, cod-liver oil or also ceramides or ceramide-like compounds etc. It is also advantageous to choose the active ingredients from the group of refatting substances, for example purcellin oil, Eucerit® and Neocerit®.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention without limiting it. The numerical values in the examples refer to percentages by weight, based on the total weight of the respective preparations.

EXAMPLE 1

|  | % by weight |
|---|---|
| PEG-22 Dodecyl glycol copolymer | 1.5 |
| PEG-45 Dodecyl glycol polymer | 1.5 |
| Isohexadecane | 12.0 |
| Isoeicosane | 5.0 |
| Glycerol | 3.0 |
| Chitosan | 1.0 |
| Lactic acid | 0.6 |
| NaCl | 1.0 |
| Perfume, preservatives, dyes, antioxidants | q.s |
| Water | ad 100.00 |

EXAMPLE 2

|  | % by weight |
|---|---|
| PEG-22 Dodecyl glycol copolymer | 1.5 |
| PEG-45 Dodecyl glycol polymer | 1.5 |
| Dicaprylyl ether | 4.5 |
| Octyl cocoate | 6.5 |
| Glycerol | 3.0 |
| Cationic starch derivatives | 1.0 |
| $MgSO_4$ | 0.7 |
| Perfume, preservatives, dyes, antioxidants | q.s. |
| Water | ad 100.0 |

EXAMPLE 3

|  | % by weight |
|---|---|
| PEG-22 Dodecyl glycol copolymer | 1.5 |
| PEG-45 Dodecyl glycol polymer | 1.5 |
| Isopropyl stearate | 4.0 |
| $C_{12-14}$-Alkyl benzoate | 4.0 |
| Octyl palmitate | 4.0 |
| Glycerol | 3.0 |
| Cationic cellulose derivatives | 1.0 |
| Perfume, preservatives, dyes, antioxidants | q.s. |
| Water | ad 100.0 |

EXAMPLE 4

|  | % by weight |
|---|---|
| PEG-45 Dodecyl glycol polymer | 1.5 |
| $C_{12-15}$-Alkyl benzoate | 10.0 |
| Glycerol | 3.0 |
| $MgSO_4$ | 0.7 |
| Guar-hydroxypropyltrimethylammonium chloride | 0.65 |
| Perfume, preservatives, dyes, antioxidants | q.s. |
| Water | ad 100.0 |

EXAMPLE 5

|  | % by weight |
|---|---|
| PEG-22 Dodecyl glycol copolymer | 0.9 |
| Octyl cocoate | 10.0 |
| Glycerol | 3.0 |
| $MgSO_4$ | 0.7 |
| Sodium polystyrenesulfonate | 1.5 |
| Perfume, preservatives, dyes, antioxidants | q.s. |
| Water | ad 100.0 |

EXAMPLE 6

|  | % by weight |
|---|---|
| PEG-22 Dodecyl glycol copolymer | 2.0 |
| Isopropyl stearate | 10.0 |
| Glycerol | 3.0 |
| Cationic cellulose derivatives | 1.0 |
| $MgSO_4$ | 0.7 |
| Perfume, preservatives, dyes, antioxidants | q.s. |
| Water | ad 100.0 |

EXAMPLE 7

|  | % by weight |
|---|---|
| PEG-45 Dodecyl glycol polymer | 2.25 |
| Dicaprylyl carbonate | 10.0 |
| Glycerol | 3.0 |
| NaCl | 1.0 |
| Sodium polystyrenesulfonate | 1.5 |
| Perfume, preservatives, dyes, antioxidants | q.s. |
| Water | ad 100.0 |

EXAMPLE 8

|  | % by weight |
|---|---|
| PEG-45 Dodecyl glycol polymer | 1.0 |
| Dicaprylyl ether | 10.0 |
| Glycerol | 3.0 |
| $MgSO_4$ | 0.7 |
| Cationic cellulose derivatives | 1.0 |
| Perfume, preservatives, dyes, antioxidants | q.s. |
| Water | ad 100.0 |

EXAMPLE 9

|  | % by weight |
|---|---|
| PEG-22 Dodecyl glycol copolymer | 2.0 |
| Butylene glycol dicaprylate/dicaprate | 10.0 |
| Glycerol | 3.0 |
| Lactic acid | 1.0 |
| Chitosan | 1.5 |

-continued

| | % by weight |
|---|---|
| MgSO$_4$ | 0.7 |
| Perfume, preservatives, dyes, antioxidants | q.s. |
| Water | ad 100.00 |

EXAMPLE 10

| | % by weight |
|---|---|
| PEG-45 Dodecyl glycol polymer | 0.75 |
| Dioctylcylohexane | 10.0 |
| Glycerol | 3.0 |
| Chitosan | 1.5 |
| Glycolic acid | 1.0 |
| MgSO$_4$ | 0.7 |
| Perfume, preservatives, dyes, antioxidants | q.s. |
| Water | ad 100.0 |

What is claimed is:

1. A water-in-oil emulsion comprising
   (a) an aqueous phase with a content of water and optionally water soluble substances totalling at least 70% by weight, and with a content of lipids, emulsifiers and lipophilic constitutents totalling at most 20% by weight, in each case based on the total weight of the aqueous phase,
   (b) a lipid phase whose polarity is between 20 and 45 mN/m,
   (c) at least one interface-active substance which is/are polyethers of an oligomeric or polymeric molecular unit B, the monomers of which are branched α,ω-alkylene glycols (α,ω-dihydroxyalkanes) having 3–25 carbon atoms and two units A composed of polyoxyethylene groups, where the molecular units A and B are linked together according to the scheme A-O-B-O-A via ether groups,
   (d) at least one cationic polymer.

2. The emulsion as claimed in claim 1, wherein the polyether(s) is/are chosen such that the polyoxyethylene component has the basic structure:

$$H{-}(O{-}CH_2{-}CH_2)_n{-}OH$$

where n assumes values from 10–200.

3. The emulsion as claimed in claim 1, wherein the polyether(s) is/are chosen such that the component of the branched or unbranched α, ω-alkylene glycols has the basic structure:

$$HO{-}(R{-}O)_p{-}H$$

where p assumes values between 2 and 200.

4. The emulsion as claimed in claim 1, wherein the polyether(s) is/are chosen from the group of substances of the following structure:

$$H{-}(O{-}CH_2{-}CH_2)_n{-}O{-}R'{-}(O{-}CH_2{-}CH_2)_m{-}OH$$

where n and m, independently of one another, are chosen from the range 10–200.

5. The emulsion as claimed in claim 1, wherein PEG-45 (dodecyl glycol) copolymer and/or PEG-22 (dodecyl glycol) copolymer are chosen as polyether.

6. The emulsion as claimed in claim 1, wherein the total amount of the polyethers is in the range of 0.1–30% by weight, based on the total weight of the emulsion.

7. The emulsion as claimed in claim 1, wherein the cationic polymer(s) is/are selected from the group consisting of cationic cellulose derivatives, cationic starch, copolymers of diallylammonium salts and acrylamides, quaternized vinylpyrrolidone/vinylimidazole polymers, condensation products of polyglycols and amines, quaternized collagen polypeptides, quaternized wheat polypeptides, polyethyleneimine, cationic silicone polymers, copolymers of adipic acid with dimethylaminohydroxypropyldiethylene-triamine, copolymers of acrylic acid with dimethyldiallylammonium chloride, polyaminopolyamides, cationic chitin derivatives, cationic guar gum, quaternized ammonium salt polymers, and cationic biopolymers.

8. The emulsion of claim 2 wherein n assumes values from 20–70.

9. The emulsion of claim 4 wherein n and m, independently of one another, are chosen from the range 20–70.

10. The emulsion as claimed in claim 6, wherein the total amount of the polyethers is in the range of 0.25–5.0% by weight, based on the total weight of the emulsion.

11. The emulsion as claimed in claim 6, wherein the total amount of the polyethers is in the range of 0.75–3.5% by weight, based on the total weight of the emulsion.

12. The emulsion of claim 7 wherein the cationic biopolymer is chitosan.

* * * * *